US010303843B2

(12) United States Patent
Bitran et al.

(10) Patent No.: US 10,303,843 B2
(45) Date of Patent: May 28, 2019

(54) COMPUTING SYSTEM FOR IDENTIFYING HEALTH RISK REGIONS (71) Applicant: Microsoft Technology Licensing, LLC, Redmond, WA (US)

(72) Inventors: Hadas Bitran, Ramat Hasharon (IL); Todd Holmdahl, Redmond, WA (US); Eric Horvitz, Kirkland, WA (US); Desney S. Tan, Kirkland, WA (US); Dennis Paul Schmuland, Redmond, WA (US); Adam T. Berns, Issaquah, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 732 days.

(21) Appl. No.: 14/970,038

(22) Filed: Dec. 15, 2015

(65) Prior Publication Data
US 2017/0039339 A1 Feb. 9, 2017

Related U.S. Application Data (60) Provisional application No. 62/202,137, filed on Aug. 6, 2015.

(51) Int. Cl.
G16H 50/30 (2018.01)
G06F 19/00 (2018.01)
G16H 50/80 (2018.01)

(52) U.S. Cl.
CPC ............ G06F 19/00 (2013.01); G16H 50/30 (2018.01); G16H 50/80 (2018.01)

(58) Field of Classification Search
CPC .. G06F 19/00; G06F 19/3418; G06F 19/3456; G16H 50/20; G16H 50/30; G16H 10/60
(Continued)

(56) References Cited

U.S. PATENT DOCUMENTS 8,560,479 B2 10/2013 Bosworth et al.
2007/0132597 A1* 6/2007 Rodgers ................. G06F 19/00
340/573.1

(Continued)

OTHER PUBLICATIONS

Schmuland, et al., "Consumer Engagement Reference Architecture (CERA) for Health Plans", Published on; Mar. 2007 Available at: https://msdn.microsoft.com/en-us/library/bb964538.aspx.
(Continued)

Primary Examiner — Reginald R Reyes
(74) Attorney, Agent, or Firm — Alleman Hall Creasman & Tuttle LLP (57) ABSTRACT A computing system is provided. The computing system includes an electronic personal assistant application server configured to determine a target location for a selected user and time, determine a group of other registered users who are or will be physically present at the target location at or around the predetermined time, determine group health data representing a health condition of the group of other registered users, the group health data being determined based on anonymous medical records statistics for the group of other registered users, the anonymous medical records statistics including biometric data sensed by at least one biometric sensor associated with at least one user computing device of one of the other registered users, identify a health risk level for the target location using the group health data, and generate an activity warning for the target location based on the health risk level.

20 Claims, 6 Drawing Sheets (58) Field of Classification Search
USPC .......................................................... 705/3
See application file for complete search history.

(56) References Cited

U.S. PATENT DOCUMENTS

| | | | |
|---|---|---|---|
| 2008/0021731 A1* | 1/2008 | Rodgers | A61B 5/1113 705/2 |
| 2008/0306763 A1 | 12/2008 | James | |
| 2009/0216558 A1 | 8/2009 | Reisman et al. | |
| 2011/0184250 A1 | 7/2011 | Schmidt et al. | |
| 2012/0101847 A1 | 4/2012 | Johnson et al. | |
| 2012/0244886 A1 | 9/2012 | Blom et al. | |
| 2013/0012789 A1 | 1/2013 | Horseman | |
| 2013/0024205 A1 | 1/2013 | Lyle et al. | |
| 2013/0024211 A1 | 1/2013 | Monteforte et al. | |
| 2014/0046679 A1 | 2/2014 | Wentz et al. | |
| 2014/0114677 A1 | 4/2014 | Holmes | |
| 2014/0155705 A1* | 6/2014 | Papadopoulos | G06F 19/00 600/301 |
| 2015/0035675 A1 | 2/2015 | Gunaratnam et al. | |

OTHER PUBLICATIONS

"New Microsoft HealthVault Applications and Devices Unveiled", Published on: Jun. 9, 2008 Available at: http://news.microsoft.com/2008/06/09/new-microsoft-healthvault-applications-and-devices-unveiled/.

"New Alert App Is First To Implement Real-Time Apple Health Kit Data", Published on: Jul. 19, 2015 Available at: http://www.inquisitr.com/2266113/new-alert-app-is-first-to-implement-real-time-apple-health-kit-data/.

"HealthKit", Published on: Mar. 15, 2015 Available at: https://developer.apple.com/healthkit/.

"Consumer Decision Journey: Health and Wellness", Retrieved on: Aug. 17, 2015 Available at: http://advetising.microsoft.com/en/cl/6933/consumer-decision-journey-health-and-wellness.

Tozzi, et al., "Bloomberg: Your Google searches could help the FDA find drug side-effects", Published on: Jul. 15, 2015 Available at; http://www.bloomberg.com/news/articles/2015-07-15/your-google-searches-could-help-the-fda-find-drug-side-effects.

Buytendijk, F. et al., "Summary and Link to Purchase 'Analytics Gets Personal with the Quantified Self'," Gartner, Inc. Website, Available Online at https://www.gartner.com/doc/2487617?ref=ddisp, May 17, 2013, 2 pages.

McIcintyre, A. et al., "Summary and Link to Purchase 'Market Trends: Enter the Wearable Electronics Market With Products for the Quantified Self'," Gartner, Inc. Website, Available Online at https://www.gartner.com/doc/2537715?ref=ddisp, Jul. 1, 2013, 2 pages.

Gotta, S., "Summary and Link to Purchase 'Technology Overview: Quantified Self'," Gartner, Inc. Website, Available Online at https://www.gartner.com/doc/2591327?ref=ddisp, Sep. 17, 2013, 2 pages.

Dunbrack, L., "Abstract and Link to Purchase 'Perspective: The Consumer Experience—Why Consumers Stop Using Fitness Trackers'," IDC Research, Inc. Website, Available Online at http://www.idc.com/getdoc.jsp?containerId=HI249613, Jun. 2014, 2 pages.

Gierl, L. et al. "Geomedical warning system against epidemics", In the International Journal of Hygiene and Environmental Health, vol. 208, Issue 4, Jul. 20, 2005, 11 pages.

ISA European Patent Office, International Search Report and Written Opinion Issued in PCT Application No. PCT/US2016/043223, dated Nov. 8, 2016, WIPO, 10 pages.

* cited by examiner

COMPUTING SYSTEM FOR IDENTIFYING HEALTH RISK REGIONS

CROSS REFERENCE TO RELATED APPLICATIONS

This application claims priority to U.S. Patent Application No. 62/202,137 entitled "COMPUTING SYSTEM FOR IDENTIFYING HEALTH RISK REGIONS", filed Aug. 6, 2015, the entirety of which is hereby incorporated herein by reference.

BACKGROUND

Many exogenous factors can negatively impact a person's health. For instance, communicable diseases such as influenza and the common cold can rapidly spread throughout groups of people who gather in a location, such as coworkers in an office, classmates in a classroom, diners in a restaurant, or passengers on an airplane. While measures can be taken, such as frequent hand washing and getting plenty of sleep, to improve one's odds of not getting sick, even the most careful measures will occasionally fail, and communicable diseases inexorably spread, particularly as the seasons turn colder and people spend more time indoors. The resultant cost to individuals and society as a whole in lost productivity and suffering is immeasurable.

SUMMARY

To address the above issue, a computing system is provided. According to one aspect, the computing system may include an electronic personal assistant application server including a processor configured to determine a target location for a selected registered user at a predetermined time, determine a group of other registered users who are or will be physically present at the target location at the predetermined time or within a time range prior to the predetermined time, determine group health data representing a health condition of the group of other registered users, the group health data being determined based on anonymous medical records statistics for the group of other registered users stored in an aggregated medical records statistics database in communication with the electronic personal assistant application server, the anonymous medical records statistics including biometric data sensed by at least one biometric sensor associated with at least one user computing device of one of the other registered users, identify a health risk level for the target location using the group health data, generate an activity warning for the target location based on the health risk level, and send the activity warning to a client computing device of the selected registered user, the activity warning configured for presentation on the client computing device.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

A computing system designed to positively impact both the health of an individual as well as the health of an ad hoc group of people is described herein. The computing system includes an electronic personal assistant application server configured to determine a selected registered user will be in a common location with a group of other registered users at a specified time. For instance, the system may ascertain that a number of users will be in a conference room during an established meeting time. The computing system also gathers aggregated medical records statistics corresponding to the group of other registered users. For instance, the computing system may gather statistics indicating that some of the members of the registered user group are likely to have influenza, a common cold, chickenpox, and/or other infectious diseases. The statistics can include biometric data (e.g., body temperature, heart rate, blood oxygen saturation, etc.,) sensed by a user device such as a mobile computing device (e.g., smartphone, wearable device, etc.,) as well as medical records of users in the group. These statistics can then be used to ascertain group health data representing a health condition (e.g., infectious disease condition) of the group of registered users. From the group health data a health risk level for the selected registered user can be determined by the electronic personal assistant application server. Subsequently, an activity warning may be generated by the electronic personal assistant application server based on the health risk level. The activity warning may then be transferred to the selected user's computing device. In this way, large sets of group health statistics can be leveraged to provide granular health alerts to a selected user for specified regions and times. Consequently, users can be provided with useful health alerts related to their daily activity. In particular, the activity warning can prompt a user to take mitigating actions to reduce their exposure to high risk regions. For example, a user may avoid or reschedule a trip to the gym when the electronic personal assistant application server alerts the user that there is a considerable risk of catching the flu at the gym during their scheduled workout time. Numerous other use case scenarios are discussed herein. As a result, a user's health risk can be reduced to improve their health and well-being.

Figure 1:
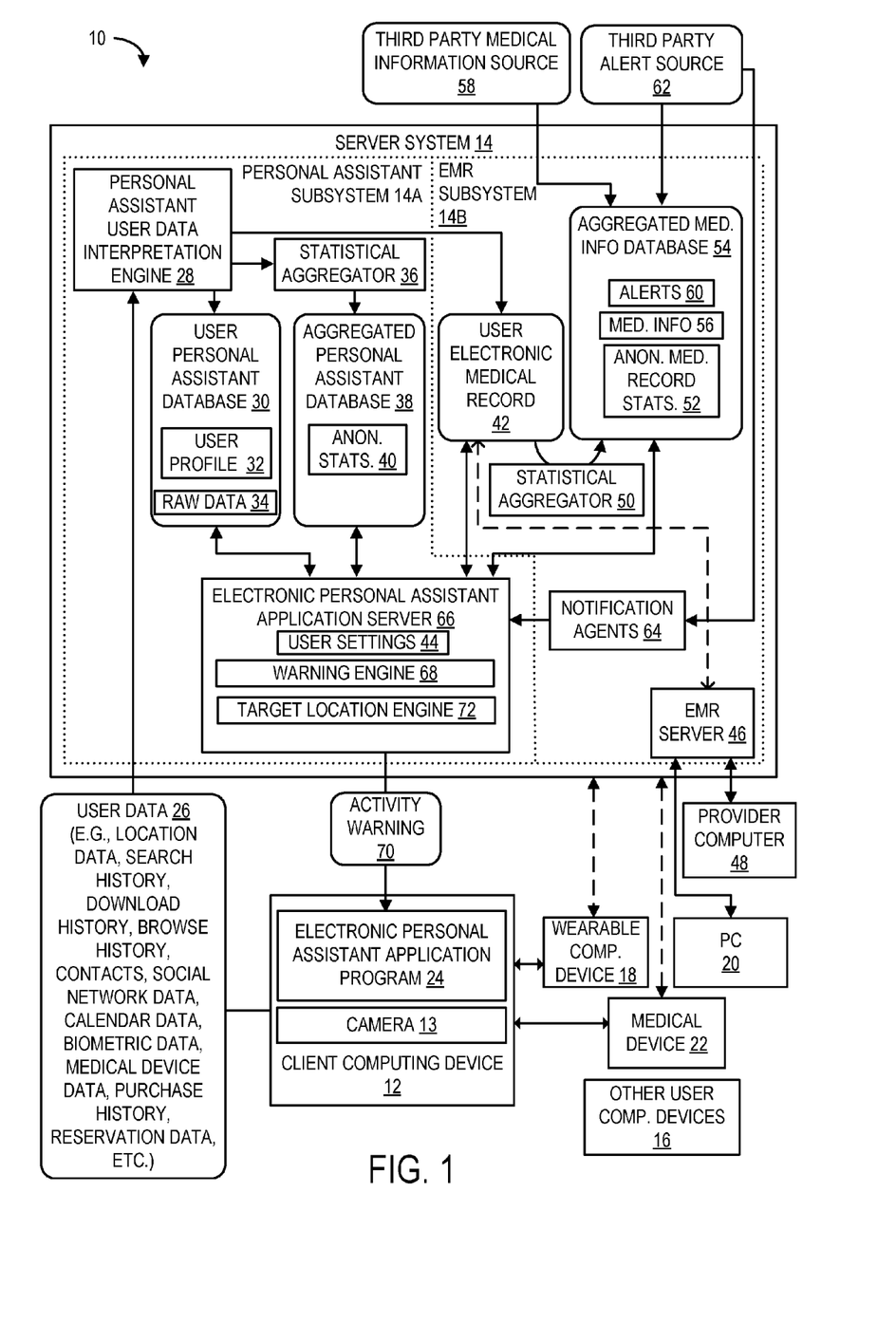
FIG. 1 shows a depiction of a computing system, according to one embodiment of the present disclosure.

FIG. 1 illustrates a computing system 10 according to one embodiment of the present disclosure. As shown, computing system 10 includes a client computing device 12, which, for example, may take the form of a smart phone or tablet computing device, configured to communicate via a computer network with a server system 14. The client computing device 12 may include a camera 13 (e.g., infrared camera). Computing system 10 may also include other client computing devices 16 configured to communicate with the server system 14 directly through a network connection or indirectly through the client computing device 12. The other client computing devices 16 may include a wearable computing device 18, which may take the form of a wrist mounted device or head mounted device, a personal computer 20, which may take the form of a laptop or desktop computer, and a computerized medical device 22, such as a computerized pulse oximeter, electronic inhaler, electronic insulin delivery device, electronic blood sugar monitor, etc. Herein, where functions of the client computing device 12 are described, it will be appreciated that any of the other client computing devices 16 may function in the same manner, unless the specific form factor of the device is mentioned explicitly.

Client computing device 12 is configured to execute an electronic personal assistant application program 24. It will be appreciated that other instances of the electronic personal assistant application program 24 may be executed on the other client computing devices 16 as well, all of which are associated with a user account on server system 14. Subject to authorization by a registered user, the electronic personal assistant program is configured to passively monitor various user data 26 on the client computing device 12 and other client computing devices 16. Thus, the registered user may opt in to various types of data collection through the server system 14. In particular, the user may opt in during registration in the server system 14 such as when registering with electronic personal assistant application server 66. In this way, data only may be gathered when a user has authorized such data collection, alleviating privacy concerns. Moreover, the system can also register a group of other registered users and prompt the users to opt in to data collection in a similar manner. Registration of a user may include generation of a password, username, etc. For instance, the user may sign up for the electronic personal assistant application program 24 via a graphical user interface presented on the client computing device 12 prompting the user to generate a username and password and select application preferences. However, numerous registration scenarios have been contemplated.

The user data 26 may include location data, search history, download history, browsing history, contacts, social network data, calendar data, biometric data, medical device data, purchase history, reservation data, etc.

Specific examples of these various types of user data 26 will now be described. Location data may include for example, GPS coordinate data (latitude and longitude) obtained by a GPS receiver implemented on any client computing device, an identifier such as an IP address and/or Wi-Fi access point identifier that can be resolved to a generalized geographic location, a user check-in at a location via a social network program, etc. Search history may include a user's search queries entered in a search engine interface such as a browser displaying a search engine web page or a search application executed on the client computing device. The download history may include, for example, applications or files downloaded from a download website or server, including documents, songs, videos, etc. The browse history may include a list of websites, and particular pages within websites visited by a user using a browser executed on the client computing device. The browse history may also include in-application browsing of application specific databases, such as a shopping application that is configured to enable a user to browse a vendor's catalog. The contacts include names and contact information for individuals or organizations saved in a user contact database on client computing device 12, or retrieved from an external site, such as a social network website. The social network data may include a user's friends list, a list of social network entities "liked" by the user, check-ins made by the user at locations via a social network program, etc.

The user data 26 may also include biometric data may include a variety of data sensed by sensors on client computing device 12, wearable computing device 18, or other client computing devices 16, such as pedometer information, heart rate, blood pressure, duration and timing of sleep cycles, body temperature, galvanic skin response, blood oxygen saturation, etc. Therefore, the computing devices may include body temperature sensors, pulse sensors, pulse oximeters, blood pressure sensors, etc. Specifically in one example, the camera in the client computing device 12 may be used to determine a body temperature of the user. Additional biometric data is discussed below in relation to the wristwatch embodiment of the wearable computing device. The biometric data may also include data gathered from medical device 22. Such data may include, for example, inhaler usage data from an electronic inhaler device, blood sugar levels from an electronic blood sugar monitor, insulin pumping data from an electronic insulin pump, pulse oximetry data from an electronic pulse oximeter, etc.

The user data 26 can also include purchase history may include information gleaned from an ecommerce transaction between the client computing device 12 and an ecommerce platform, regarding products purchased by a user, including product descriptions, time and date of purchase, price paid, user feedback on those purchases, reservation data (e.g., travel service reservation data) etc. It will be appreciated that these specific examples are merely illustrative and that other types of user data specifically not discussed above may also be monitored. The travel service reservation data can include flight reservations, hotel reservations, dining reservations, etc. For instance, a user may book a flight online and the flight information may be downloaded by the personal assistant user data interpretation engine 28.

User data 26 is transmitted from the electronic personal assistant application program 24 to the personal assistant interpretation engine 28 executed on server system 14. The personal assistant user data interpretation engine 28 performs various operations on the received user data 26, including storing copies of the raw data 34 of the user data 26 in the user personal assistant database 30 (a database stored in a mass storage device of the server system 14), making inferences based upon the received user data 26 to thereby fill out a user profile 32 for the user, passing some of the user data 26 for each individual user to a statistical aggregator 36, which computes anonymous personal assistant statistics 40 based on information received from all users of the server system and stores these anonymized statistics in the aggregated personal assistant database 38 (another databases stored in a mass storage device of the server system 14), and passing a filtered subset of the user data to the user electronic medical record 42 based on user settings 44 in the electronic personal assistant application server 66.

As a specific example, the user profile 32 may include inferred data from the user data 26 regarding the demographic data on the age, gender, race and ethnicity, and place of residence of the user, geographic travel history of the user, place of employment of the user, family unit of the user, family medical history, past medical history of the user, preexisting medical conditions of the user, current medications of the user, allergies of the user, surgical history, past medical screenings and procedures, past hospitalizations and visits, social history (alcohol, tobacco, and drug use, sexual history and habits, occupation, living conditions), health maintenance information (exercise habits, diet information, sleep data, vaccination data, therapy and counseling history), health provider preferences, and health benefits information.

User electronic medical records can be secure electronic records stored in a database in a mass storage device associated with server system 14. Typically, data is populated within the electronic medical record for each user by a healthcare provider using provider computer 48. Provider computer 48 interacts with secure electronic medical record (EMR) server 46, which in turn stores and retrieves the data in the user electronic medical record 42. The EMR server is configured to communicate with secure channels (e.g., HTTPS and TLS), and store data in encrypted form. Further, the EMR server is configured to control access to the user electronic medical record such that only authorized healthcare providers can make entries and alter certain provider-controlled fields of the medical record. Provider controlled fields may include many of the same types of data included in the user profile, but which are confirmed with the user by the provider and entered into the medical record by the provider rather than inferred by computer algorithms, thus the accuracy and provenance of the data in the EMR may be greater than the user profile 32. Specific examples of data that may be stored in the provider controlled portion of the user electronic medical record include demographic data on the age, gender, race and ethnicity, and place of residence of the user, geographic travel history of the user, place of employment of the user, family unit of the user, family medical history, past medical history of the user, preexisting medical conditions of the user, current medications of the user, allergies of the user, surgical history, past medical screenings and procedures, past hospitalizations and visits, social history (alcohol, tobacco, and drug use, sexual history and habits, occupation, living conditions), health maintenance information (exercise habits, diet information, sleep data, immunization data (e.g., vaccination data), therapy and counseling history), health provider preferences, health benefits information, test results, and genetic profile of the user.

Other fields within the user electronic medical record are user-controlled, such that authorized persons including the patient who is the subject of the medical record can make entries in the medical record. Further, the user may adjust user settings 44 to allow the personal assistant user data interpretation engine 28 to programmatically update the user-controlled fields of the user electronic medical record with either raw data 34 or inferred data in user profile 32 derived from user data 26. In this way the medical record may be programmatically updated to include medical device data such as inhaler usage, blood sugar monitoring levels, insulin pump usage, etc., and biometric data such as heart rate and blood pressure history, sleep history, body temperature, galvanic skin response, etc.

A statistical aggregator 50 is provided to generate anonymized medical records statistics 52 based on the stored user electronic medical records of an entire user population or an ad hoc group thereof, and store the anonymized medical records statistics in aggregated medical information database 54. The statistical aggregator may aggregate the user electronic medical record 42 as well as other medical records to form the anonymized medical records statistics 52. In this manner, statistics may be stored for all manner of user populations. For example, a percentage of the population who live within a defined geographical region and have been diagnosed with a certain medical condition (such as influenza) may be identified, and data about this subset of persons may be compared to identify risk factors.

Medical information 56 aggregated from third party medical information sources 58 and alerts 60 from third party alert sources 62 are also stored within the aggregated medical information database 54. Examples of medical information 56 includes current practices and procedures, differential diagnostic information that medical professionals use to distinguish between possible diagnoses for a given set of symptoms, descriptions of medical conditions including diseases and syndromes, and their associated symptoms, information on standardized medical screenings recommended by age and gender of the patient, information on standardized vaccination schedules recommended for children and adults, medical conditions associated with certain genetic profiles, etc. Examples of third party medical information sources 58 include medical publishers, professional medical organizations. Examples of alerts include reports from governmental and non-governmental organizations that report the occurrence of disease in particular geographic regions, including the boundaries of the geographic region, the type of disease reported, the number of persons affected, the mortality statistics associated with the affected persons, information about the incubation period and period of contagiousness for the disease, and any travel restrictions or recommended restrictions to the affected geographic region, etc. These alerts may be from a country's center for disease control, state or county health department, a company, a school district, a hospital, etc. Alerts 60 from third party alert sources 62 may also be received by notification agents 64 within server system 14.

The electronic personal assistant application server 66 includes a target location engine 72 configured to determine a target location of both a selected registered user and a group of other registered users. The target location may be determined based on a number of data inputs such as data in the user personal assistant database 30 and/or the aggregated personal assistant database 38. The way in which the target location may be determined is discussed in greater detail herein.

Additionally, the server system 14 is also configured to instruct a warning engine 68 of the electronic personal assistant application server 66 to send an activity warning 70 to the client computing device 12. The activity warning 70 may be an alert related to a health risk level for the target location determined by the target location engine 72 at a predetermined period of time or time range. The health risk level may be determined based on a number of inputs such as health data in the user personal assistant database 30, aggregated personal assistant database 38, and/or aggregated medical information database 54, discussed in greater detail herein.

As illustrated, the server system 14 may be divided into a personal assistant subsystem 14A and an EMR subsystem 14B. However, in other examples the server system 14 may not be divided into these subsystems or may be apportioned into different subsystems. The components, devices, databases, etc., included in the personal assistant subsystem 14A may include the personal assistant user data interpretation engine 28, statistical aggregator 36, user personal assistant database 30, aggregated personal assistant database 38, and/or electronic personal assistant application server 66. The components, devices, databases, etc., included in the EMR subsystem 14B may include aggregated medical information database 54, user electronic medical record 42, statistical aggregator 50, notification agents 64, and EMR server 46.

Figure 2:
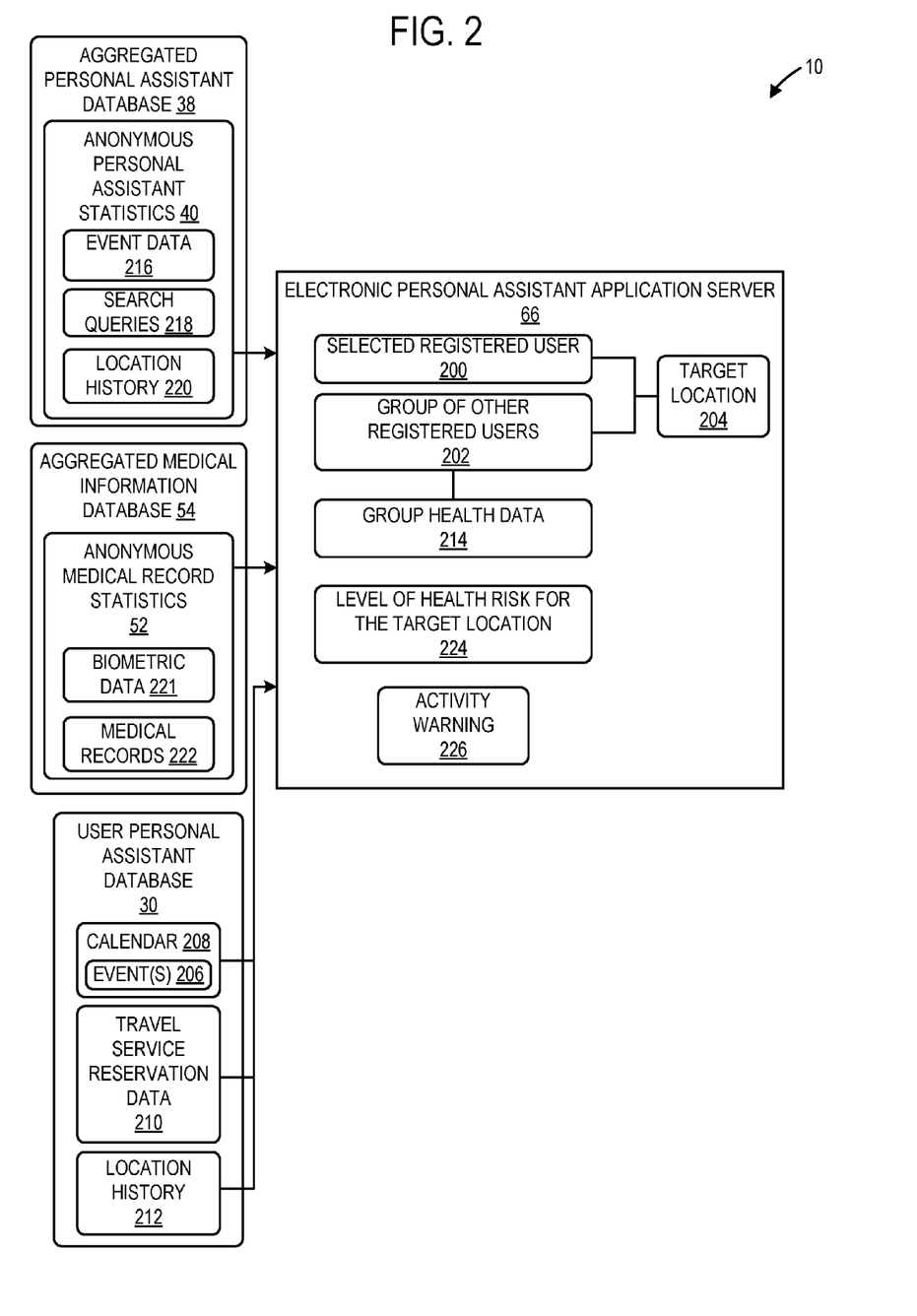
FIG. 2 illustrates an activity warning feature of the computing system shown in FIG. 1.

FIG. 2 shows a diagram of an activity warning features of the computing system 10. As shown, the electronic personal assistant application server 66 determines a selected registered user 200 and a group of other registered users 202 predicted to be near or at a common target location 204 at predetermined time or within a time range prior to the predetermined time. Therefore, the group of other registered users 202 is an ad hoc group of users associated with the target location 204.

The target location may be a current or future predicted location of the registered users. The target location may be expressed as coordinates, coordinates ranges, address, etc. It will also be appreciated that the target location may be a current or future prediction location.

When the target location is the current location of the selected registered user the current GPS coordinates of the client computing device 12, shown in FIG. 1, may be used as the target location. On the other hand, when the target location is a future predicted location the location may correspond to an event 206 in a calendar 208 stored in the user personal assistant database 30. For instance, a user may have a meeting scheduled in the calendar 208. Therefore, the meeting room or entire office may be the target location 204. In another example, the future predicted location may be ascertained from travel service reservation data 210 stored in the user personal assistant database 30. For instance, a user may book a plane flight and the flight information may be stored in the user personal assistant database 30. In such an example, the target location may be an airport terminal, airplane, etc. In yet another example, a user may book a hotel room and the hotel reservation data may be stored in the user personal assistant database 30. Therefore, the target location may be the entire hotel or a subsection of the hotel. Restaurant reservations may also be used to determine the target location 204. In another example, the target location may be determined from a user's past behaviors such as a location history 212 (e.g., geographical path of the user). For instance, a user may travel to a supermarket around 5 PM each weekday. Therefore, it may be inferred from this reoccurring travel pattern that the user is likely to visit the supermarket during forthcoming weekdays around 5 PM. Therefore, the target location may be the supermarket and the predetermined time may be 5 PM.

The group of other registered users 202 may be associated with the target location 204 based on data in the aggregated personal assistant database 38. The examples described above used to associate the selected registered user 200 with the target location 204 can also be used to associate each user in the group of other registered users 202 with the target location. For instance, events in a calendar of one of the users in the group of other registered users 202 may be used to associate the user with the target location 204.

The electronic personal assistant application server 66 is configured to determine group health data 214 representing a health condition of the group of other registered users 202. For instance, the health condition may be an infectious disease condition corresponding to one or more infectious diseases such as influenza, chickenpox, the common cold, measles, Ebola, etc. In such an example, the group health data may include data indicating a percentage of users in the group likely to have an infectious disease, a probability of one or more users in the group having an infectious disease, a degree of contagiousness of one or more of the users in the group, etc.

The group health data 214 may be determined based on the anonymous medical records statistics 52 stored in the aggregated medical information database 54 and/or anonymous personal assistant statistics 40 stored in the aggregated personal assistant database 38. Additionally, the group health data 214 may be associated with the group of other registered users 202 based on common identifiers embedded in data in both the aggregated medical information database 54 and aggregated personal assistant database 38. For instance, a common alphanumeric identifier may be associated with events in a calendar of one of the users in the group of other registered users 202 and the biometric data 221 included in the anonymous medical records statistics 52. In this way, the group health data 214 can be correlated to the target location 204 and the group of other registered users 202. However, numerous suitable techniques used to link the group health data 214 to the group of other registered users 202 and therefore the target location 204 have been contemplated.

The anonymous personal assistant statistics 40 may include event data 216, search queries 218, and location history 220 (e.g., a geographical path of registered users). The event data 216 may correspond to a calendar of events associated with one or more of the users in the group of other registered users 202. For instance, a user may enter meetings, restaurant reservations, doctor appointments, group events (e.g., party, sports game, group run/ride, etc.,) into a calendar via one of the other computing devices 16, shown in FIG. 1, and then pushed to the aggregated personal assistant database 38. The search queries 218 can include search queries entered into a network browsing application (e.g., Internet browser), the electronic personal assistant application program, etc., by one or more of the users in the group of other registered users. For example, a user may search for remedies for an illness, medical facilities nearby, etc. Additionally, the location history 220 may include a path of a user/device over a predetermined period of time. For instance, the path of one of the computing devices 16, shown in FIG. 1, may be tracked at selected time intervals, continuously tracked, etc.

The anonymous medical records statistics 52 can include biometric data 221 and medical records 222. As previously discussed, the biometric data 221 may include heart rate data, body temperature data, bloody oxygen saturation data, etc. For instance, a user's body temperature, heart rate, etc., may be measured over a period of time, at selected times during the day, etc.

The medical records 222 may be associated with one or more of the users in the group of other registered users 202 and include medical history, medications, test results, and/or immunization status. As discussed above, the medical records 222 may be gathered from various sources such as the EMR server 46 and the personal assistant user data interpretation engine 28, shown in FIG. 1.

Continuing with FIG. 2, the group health data 214 may be used to determine a health risk level 224 for the target location 204. For instance, the group health data may include a level of health risk for each user in the group of other registered users 202. These health risk levels may be averaged or otherwise combined to determine the health risk level 224 for the target location 204. A numerical scale may be used to quantify the health risk level. For instance, the health risk level may be expressed as a percentage, on a numerical scale (e.g., of 1-10, 1-100,) etc. In other examples, the health risk level may be indicated via scaling expressions such as "high", "medium", and "low".

Data that can increase the health risk level related to user(s) in group of other registered users 202 can include user data indicating elevated temperature, elevated heart rate, weak/thready pulse, decreased blood oxygen saturation, search terms corresponding to health questions/infectious diseases, travel to a health care facility (e.g., hospital, nursing home, etc.), travel to a high risk area, medical records indicating sickness, medical records indicated a compromised immune system, medical records indicating a lack of vaccine immunization, etc. For example, one of the users in the group of other registered users 202 may be have a body temperature well above 98.6 degrees and may have traveled to a hospital the previous day. Therefore, the health risk level for the user may be very high. In another example, the health risk for a particular location to which the user is scheduled to travel may be based on the location history of the other users who will be gathered at the same location at the same time as the user. For example, those another user may have dined at a restaurant or participated in a meeting in a particular conference room, and on a subsequent day the computing system may determine that one or more diners in the restaurant or participants in the meeting have come down with an infectious disease, and thus was contagious during the period of time that the other user was in the same location, and thus determine that the health risk to that other user is higher. Such analysis may be performed for each of the users that are predicted to be present in the same location as the user at a future time or a predetermined period of time prior thereto, and the health risk for the location at the time of the user's visit may be measured based on the aggregate health risk associated with each of the plurality of users based in this manner on their location histories.

An activity warning 226 may be generated based on the health risk level 224. For instance, if the health risk level is greater than a predetermined threshold value the activity warning 226 may be generated. The threshold level may be automatically set by the electronic personal assistant application server 66 or may be selected based on user input. For instance, the health risk level may be expressed on a scale of 1-10 and the threshold value may be 6, 7, 8, etc. Of course, any alternative suitable scale may be used.

The activity warning 226 may be configured for presentation on a display, such as a display corresponding to the client computing device 12, shown in FIG. 1. The activity warning may include audio, visual, and/or haptic alerts. In this way, a user can be alerted of a potential health risk, enabling them to take mitigating actions to reduce their risk, if desired. Consequently, a user's overall health and well-being can be improved.

In one example, the activity warning 226 may be configured to discourage participation in the event 206 on the calendar 208. For example, the activity warning 226 may discourage participation in a meeting where a number of the attendees are deemed to have a high likelihood of having influenza, the common cold, or another easily transmissible infectious disease. In such an example, the activity warning may encourage a user to participate in another meeting at a later date deemed to have a lower infectious disease risk, or may prompt all attendees of a meeting to attend by telephone instead of in-person. In another example, generation of the activity warning 226 may trigger automatic rescheduling or cancellation of an event. For instance, if a large number of students in a class have a high probability of being infected with chickenpox a class field-trip may be cancelled or rescheduled. In this way, uninfected students can avoid exposure to a highly contagious disease. As a result, the likelihood of disease transmission between students in the class is reduced, improving the health of the class.

In another example, the activity warning 226 may be configured to notify people whom have come into contact with a person having an infectious disease while they are contagious. For instance, a number of people may attend a meeting and it may be determined after the meeting that one of the attendees was contagious with influenza during the meeting. Therefore, the remainder of the meeting attendees may be notified via activity warnings that they were exposed to a person infected with influenza after the meeting has taken place. In yet another example, activity warnings may be sent to each registered user the system has identified as coming into contact with a contagious person.

Figure 3:
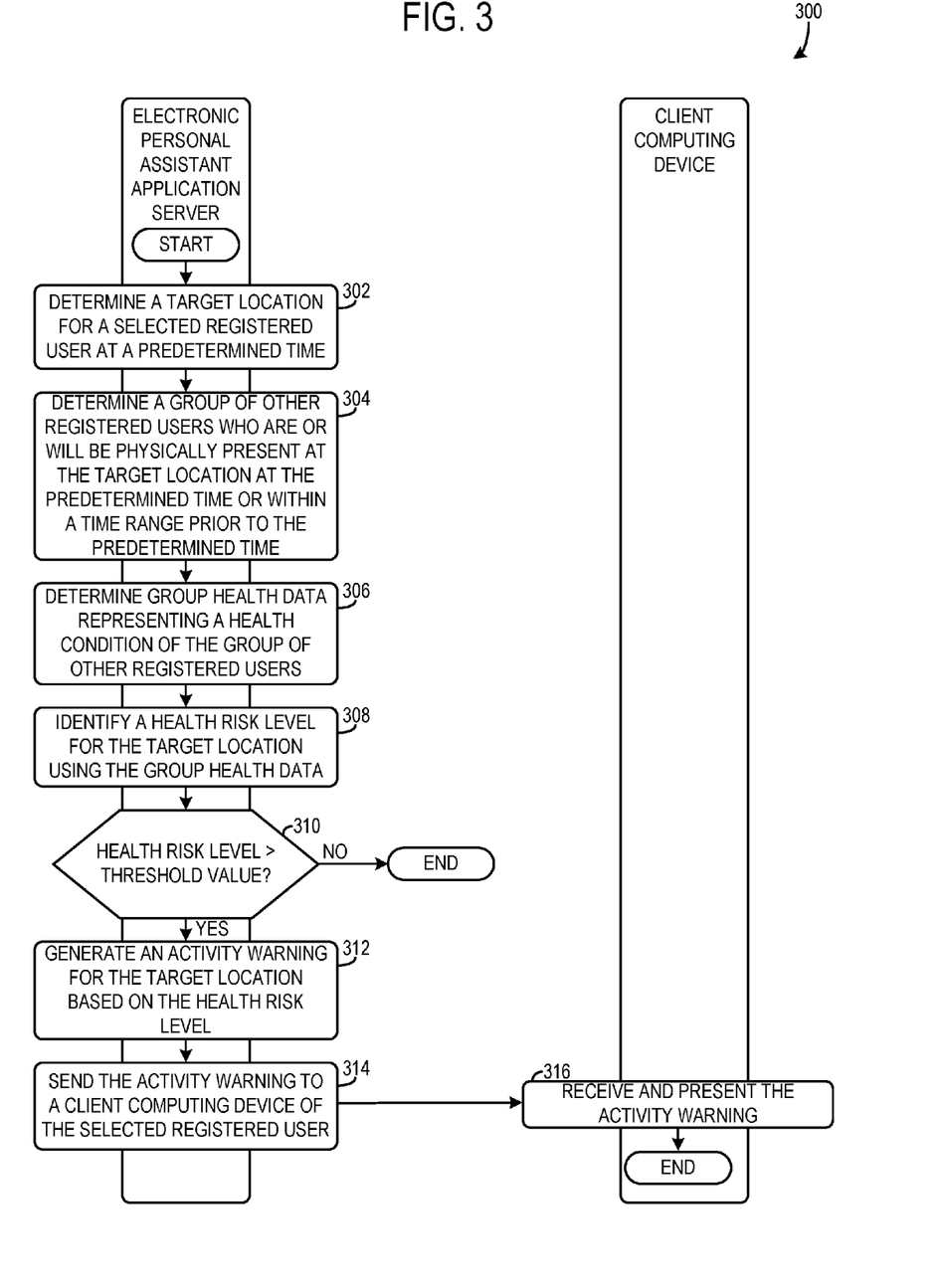
FIG. 3 shows a method for operation of a computing system, according to one embodiment of the present disclosure.

FIG. 3 shows a method 300 for operation of a computing system including an electronic personal assistant application server and a client computing device. The method 300 may be implemented via the computing system 10, electronic personal assistant application server 66, and the client computing device 12 described above with regard to FIGS. 1-2 or may be implemented by another suitable computing system, electronic personal assistant application server, and the client computing device.

At 302 the method includes determining a target location for a selected registered user at a predetermined time. As previously discussed, the target location may be a current or future predicted location and the future prediction location may be associated with an event in a calendar such as a dinner reservation, meeting, conference, etc. Therefore, the target location may be a restaurant, office building, conference room, classroom, etc. In one embodiment, the target location is a room. In another embodiment, the target location is a building. In yet another example, the target location may be a future predicted location that is ascertained from travel service reservation data. For instance, a user may purchase a train ticket online. In such an example, the target location may be the train station, a rail-car, etc. In another example, the target location may be determined from a user's a location history (e.g., geographical path). For instance, a user may travel to a bank branch around a 4 PM each Monday. Therefore, it may be inferred from this reoccurring travel pattern that the user is likely to visit the bank each Monday around 4 PM. Therefore, the target location may be the bank branch in such an example.

Next at 304 the method includes determining a group of other registered users who are or will be physically present at the target location at the predetermined time or within a time range prior to the predetermined time. For instance, the group of other registered users may include classmates, coworkers, friends, etc., determined or predicted to be at the target location. For instance, the group of other registered user's may be attendees of a meeting or other event in the selected user's calendar. In other examples, the group of other registered user's may be people attending a sporting event, a concert, etc., that the selected registered user is or will be attending. In yet another example, the selected user may book a cruise vacation and the group of other registered users may be other people who have booked a cruise vacation on the same cruise ship.

At 306 the method includes determining group health data representing a health condition of the group of other registered users. In one example, the health condition may be an infectious disease condition. For instance, the health condition may be associated with one or more infectious diseases such as influenza, chickenpox, the common cold, etc.; however, it will be appreciated that other health conditions have been contemplated. Additionally, the group health data may be determined based on anonymous medical records statistics such as biometric data (e.g., body temperature data, heart rate data, blood oxygen saturation data, etc.) sensed by biometric sensors (e.g., body temperature sensor, heart rate sensor, pulse oximeter, etc.) The anonymous medical records statistics may also include medical records of the one or more of the users in the group of other registered users such as medical history, medications, test results, and/or immunization status. The group health data may also be determined based on a location history and/or event data associated with one of the other registered users. For instance, if users in group travel to high risk regions, they may be deemed to have a higher likelihood of having an infectious disease. Additionally in one example, the group health data may be determined based on search queries corresponding to the group of other registered users. For instance, if users have searched for information related to a disease, medication related to the disease, etc., the group health data may indicate a high contagious disease risk of the users.

Next at 308 the method includes identifying a health risk level for the target location using the group health data. For example, the group health data may include a percentage of users in the group likely to have an infectious disease. This percentage may be converted into a scale of a high, medium, or low risk. In such an example, the health risk level is an infectious disease risk level. In another example, the group health data can indicate a high probability of a portion of the users having influenza and another portion of the users having a common cold. Therefore in such an example, risks of influenza and common cold transmissibility may be weighted and averaged to determine the health risk level. It will be appreciated that numerous suitable techniques may be used to determine the health risk level from the group health data.

At 310, the method determines if the health risk level greater than a threshold value. If it is determined that the health risk level is not greater than the threshold value (NO at 310) the method ends. However, if it is determined that the health risk level is greater than the threshold value (YES at 310) the method advances to 312. At 312 the method includes generating an activity warning (e.g., visual, audio, and/or haptic alert) for the target location based on the health risk level. In one example, the activity warning may discourage participation in an event on the selected registered user's calendar. In another example, the event may be automatically rescheduled and/or cancelled responsive to generation of the activity warning. Cancelling the event may include sending cancellation notices to event participant and/or deleting the event from a database. In another example, a suggestion to virtually attend the event, by telephone conference, video conference, or through holographic projection, for example, may be made.

Next at 314 the method includes sending the activity warning to a client computing device of the selected registered user. At 316 the method includes receiving the activity warning. In response to receiving the activity warning the client computing device may present the activity warning on a display. In this way, a user can be provided with a health warning that can enable the user to take actions to decrease their health risk, if desired. Consequently, the likelihood of the user contracting communicable diseases is reduced.

Figure 4:
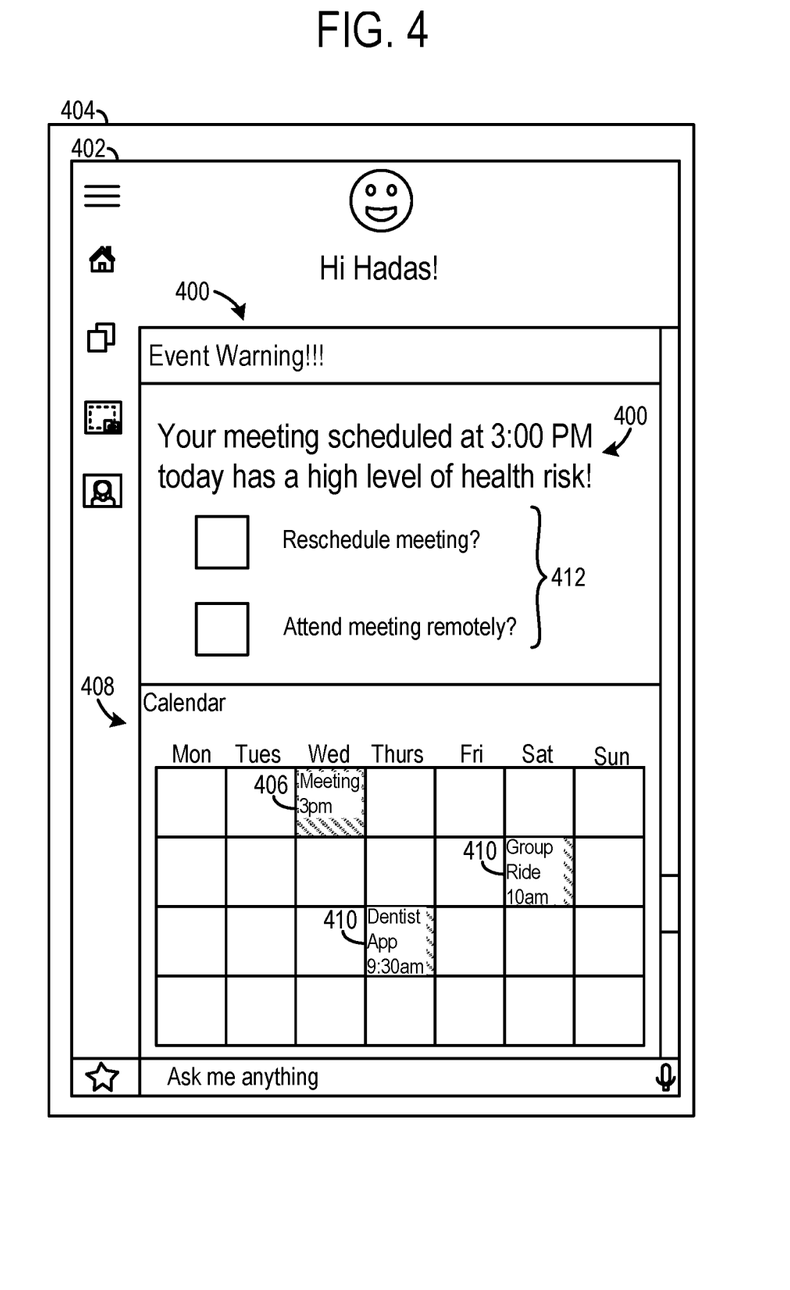
FIG. 4 shows an exemplary activity warning that may be presented on a computing device in the computing system shown in FIG. 1.

FIG. 4 illustrates an example activity warning 400 presented on a graphical user interface (GUI) 402 of a display 404. The display 404 may be included in the client computing device 12 and/or the wearable computing device 18, shown in FIG. 1. Therefore, the activity warning 400 may be sent to the display 404 by the electronic personal application server 66, shown in FIG. 1.

As illustrated in FIG. 4, the activity warning 400 alerts the user of a high health risk of a target location (i.e., meeting location). The activity warning 400 may additionally include audio and/or haptic alerts. In the depicted example, the activity warning 400 corresponds to an event 406 in a calendar 408 of events. In this way, the activity warning 400 can be associated with a user's forecasted daily activity. As shown, the calendar includes other events 410 that are not associated with the activity warning.

In the illustrated example, the activity warning 400 is configured to discourage participation via physical presence at the event 406. In this way, a user can be prompted to take actions to reduce their exposure to a region with a high level of health risk. The activity warning 400 also includes a section 412 configured to encourage the user to reschedule the meeting or attend the meeting remotely. Remote attendance may be suggested via one of the methods described above, telephone conference, video conference, or holographic projection of an avatar or representation of the user. Using such alternative measures for attendance, the meeting can still take place while reducing the health risk of the meeting participants.

Figure 5A:
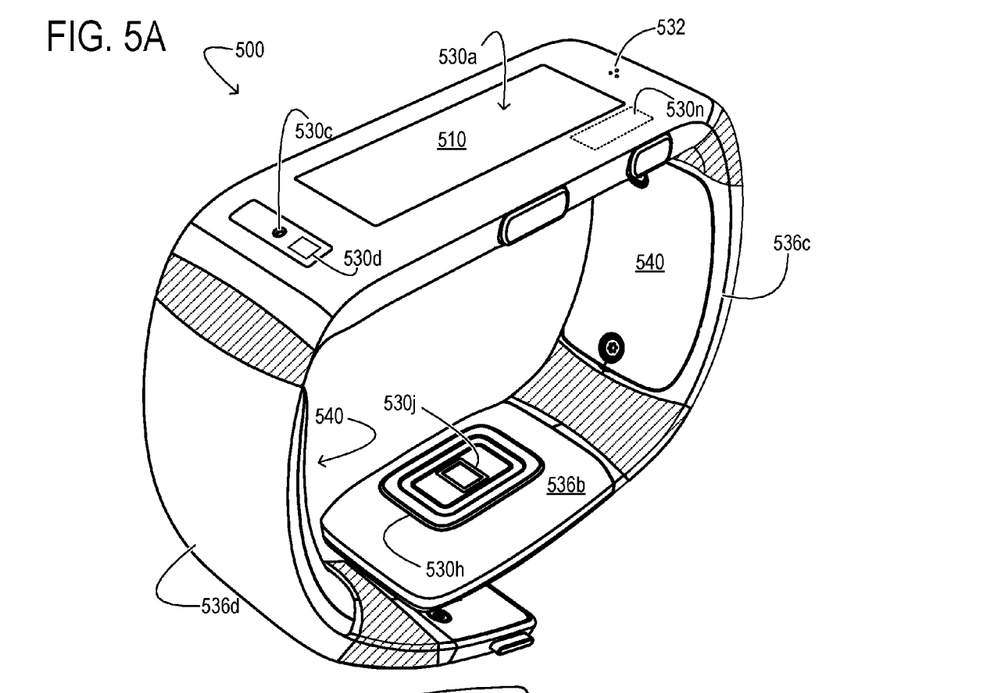
FIGS. 5A and 5B show an embodiment of a wearable computing device that may be used in conjunction with the computing system of FIG. 1.
Figure 5B:
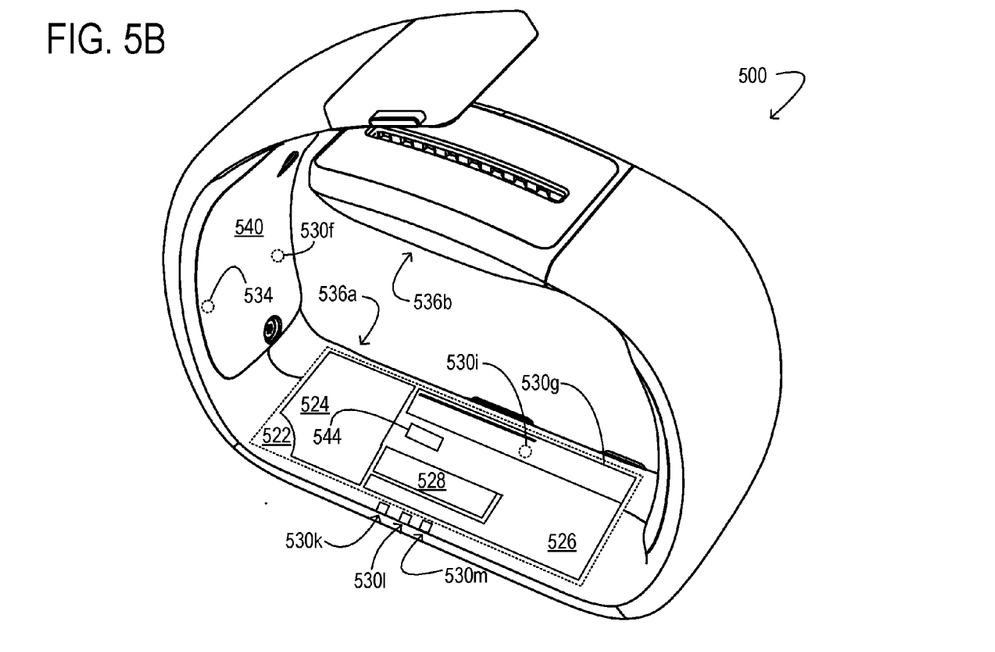

FIGS. 5A and 5B show one example of a wearable computing device 500 configured to interact with the client computing device 12 and/or server system 14, shown in FIG. 1. The device 500 illustrated in FIGS. 5A and 5B takes the form of a composite band 500 worn on a body part (e.g., wrist, ankle, bicep, etc.) of a user.

As shown in the drawings, composite band 500 may include various functional electronic components: a compute system 522, display 510, loudspeaker 532, haptic motor 534, communication device 528, and various sensors 530. In the illustrated implementation, functional electronic components are integrated into the several rigid segments of the band—viz., display-carrier module 536a, pillow 536b, and energy-storage compartments 536c and 536d.

The functional electronic components of wearable composite band 500 draw power from one or more energy-storage components 540. A battery—e.g., a lithium ion battery—is one type of energy-storage electronic component. Alternative examples include super- and ultra-capacitors. In general, energy-storage components 540 may be replaceable and/or rechargeable.

The compute system 522 is operatively coupled to display 510, loudspeaker 532, communication device 528, and to the various sensors 530. The compute system includes a computer memory device 526 to hold data and instructions, and a logic processor 524 to execute the instructions.

Display 510 may be any type of display, such as a thin, low-power light emitting diode (LED) array or a liquid-crystal display (LCD) array. Quantum-dot display technology may also be used. Suitable LED arrays include organic LED (OLED) or active matrix OLED arrays, among others.

Communication device 528 may include any appropriate wired or wireless communications componentry. In FIGS. 5A and 5B, the communications facility includes a port 544, which may be used for exchanging data between composite band 500 and other computer systems, as well as providing recharge power. The communication facility may further include two-way Bluetooth, Wi-Fi, cellular, near-field communication, and/or other radios. In some implementations, the communication facility may include an additional transceiver for optical, line-of-sight (e.g., infrared) communication.

In composite band 500, touch-screen sensor 530a is coupled to display 510 and configured to receive touch input from the wearer. In general, the touch sensor may be resistive, capacitive, or optically based.

FIGS. 5A and 5B show various other sensors 530 of composite band 500. Such sensors include microphone

530c, light sensor 530d (e.g., visible, infrared, and/or ultraviolet sensor). The body temperature of the user or other people in the vicinity of the user may be determined via the light sensor 530d. The microphone provides input to compute system 522 that may be used to measure the ambient sound level or receive voice commands from the wearer. Input from the light sensor and ambient-temperature sensor may be used to assess aspects of the wearer's environment.

FIGS. 5A and 5B show a charging contact sensor 530g arranged on display-carrier module 536a, and pillow contact sensor 530h arranged on pillow 536b. The contact sensors may include independent or cooperating sensor elements, to provide a plurality of sensory functions. For example, the contact sensors may provide an electrical resistance and/or capacitance sensory function responsive to the electrical resistance and/or capacitance of the wearer's skin. To this end, the two contact sensors may be configured as a galvanic skin-response sensor, for example. In the illustrated configuration, the separation between the two contact sensors provides a relatively long electrical path length, for more accurate measurement of skin resistance. In some examples, a contact sensor may also provide measurement of the wearer's skin temperature. In the illustrated configuration, a body temperature sensor 530i in the form a thermistor is integrated into charging contact sensor 530g, which provides direct thermal conductive path to the skin. In addition to the contact-based skin sensors described above, various types of non-contact skin sensors may also be included.

Arranged inside pillow contact sensor 530h in the illustrated configuration is a pulse rate sensor 530j (e.g., optical pulse rate sensor). The pulse rate sensor may include a narrow-band (e.g., green) LED emitter and matched photodiode to detect pulsating blood flow through the capillaries of the skin, and thereby provide a measurement of the wearer's pulse rate. In some implementations, the pulse rate sensor may also be configured to sense the wearer's blood pressure. In another example, the composite band 500 may also include a pulse oximeter 530f integrated therein. However in other examples the pulse oximeter may be a component configured to attach to a finger of the user. The pulse oximeter 530f may be configured to detect a user's blood oxygen saturation.

Composite band 500 may also include inertial motion sensing componentry, such as an accelerometer 530k, gyroscope 530l, and magnetometer 530m. The accelerometer and gyroscope may furnish inertial data along three orthogonal axes as well as rotational data about the three axes, for a combined six degrees of freedom. Data from the accelerometer and gyroscope may be combined with geomagnetic data from the magnetometer to further define the inertial and rotational data in terms of geographic orientation. Composite band 500 may also include a global positioning system (GPS) receiver 530n for determining the wearer's geographic location and/or velocity.

In some embodiments, the methods and processes described herein may be tied to a computing system of one or more computing devices. In particular, such methods and processes may be implemented as a computer-application program or service, an application-programming interface (API), a library, and/or other computer-program product.

Figure 6:
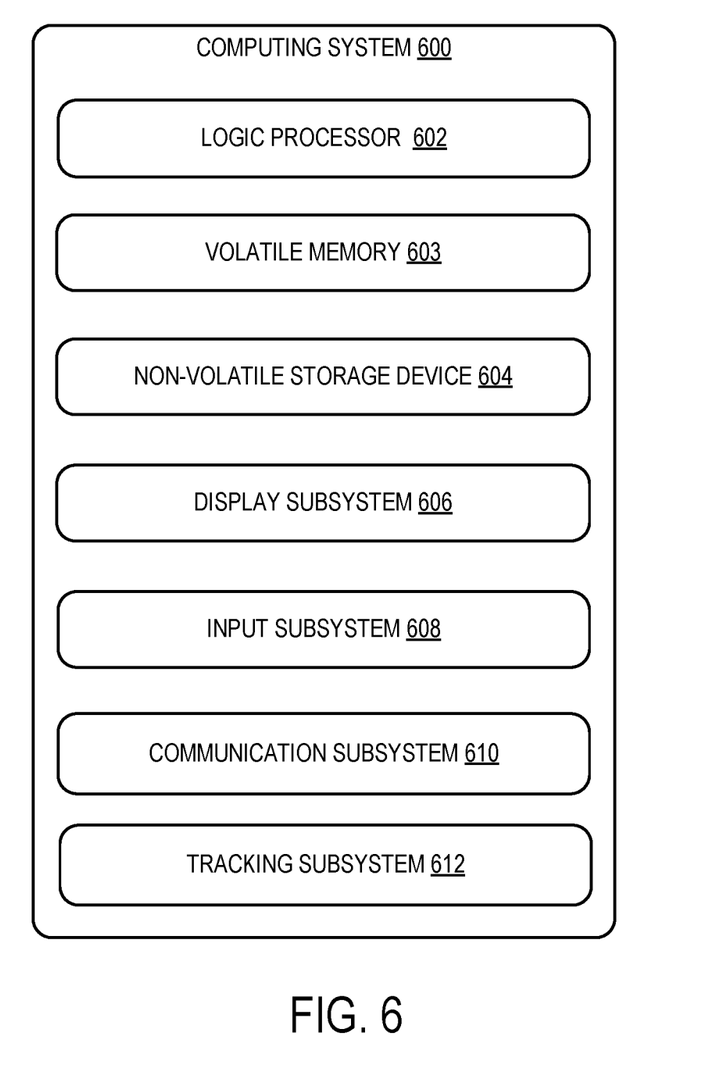
FIG. 6 shows a depiction of an exemplary computing system that may be used as any of the various computing devices of the computing system of FIG. 1.

FIG. 6 schematically shows a non-limiting embodiment of a computing system 600 that can enact one or more of the methods and processes described above. Computing system 600 is shown in simplified form. Computing system 600 may embody one or more of the servers or client computing device 12 or other client computing devices 16 of FIG. 1. Computing system 600 may take the form of one or more personal computers, server computers, tablet computers, home-entertainment computers, network computing devices, gaming devices, mobile computing devices, mobile communication devices (e.g., smart phone), and/or other computing devices, wearable computing devices such as smart wristwatches and head mounted augmented reality devices, computerized medical devices.

Computing system 600 includes a logic processor 602 volatile memory 603, and a non-volatile storage device 604. Computing system 600 may optionally include a display subsystem 606, input subsystem 608, communication subsystem 610, and/or other components not shown in FIG. 6.

Logic processor 602 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 602 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 604 includes one or more physical devices configured to hold instructions executable by the logic processors to implement the methods and processes described herein. When such methods and processes are implemented, the state of non-volatile storage device 604 may be transformed—e.g., to hold different data.

Non-volatile storage device 604 may include physical devices that are removable and/or built-in. Non-volatile storage device 604 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 604 may include nonvolatile, dynamic, static, read/write, read-only, sequential-access, location-addressable, file-addressable, and/or content-addressable devices. It will be appreciated that non-volatile storage device 604 is configured to hold instructions even when power is cut to the non-volatile storage device 604.

Volatile memory 603 may include physical devices that include random access memory. Volatile memory 603 is typically utilized by logic processor 602 to temporarily store information during processing of software instructions. It will be appreciated that Volatile memory 603 typically does not continue to store instructions when power is cut to the volatile memory 603.

Aspects of logic processor 602, volatile memory 603, and non-volatile storage device 604 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 600 typically implemented in software by a processor to perform a particular function using portions of volatile memory, which function involves transformative processing that specially configures the processor to perform the function. Thus, a module, program, or engine may be instantiated via logic processor 602 executing instructions held by non-volatile storage device 604, using portions of volatile memory 603. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 606 may be used to present a visual representation of data held by non-volatile storage device 604. The visual representation may take the form of a graphical user interface (GUI). As the herein described methods and processes change the data held by the non-volatile storage device, and thus transform the state of the non-volatile storage device, the state of display subsystem 606 may likewise be transformed to visually represent changes in the underlying data. Display subsystem 606 may include one or more display devices utilizing virtually any type of technology. Such display devices may be combined with logic processor 602, volatile memory 603, and/or non-volatile storage device 604 in a shared enclosure, or such display devices may be peripheral display devices.

When included, input subsystem 608 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 610 may be configured to communicatively couple various computing devices described herein with each other, and with other devices. Communication subsystem 610 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 600 to send and/or receive messages to and/or from other devices via a network such as the Internet.

The computing system 600 may also include a tracking subsystem 612 (e.g. GPS receiver) configured to track the location of the computing system 600. For instance, the tracking subsystem 612 may be configured to track a path of a computing device.

The subject matter of the present disclosure is further described in the following paragraphs. According to one aspect a computing system is provided. The computing system includes an electronic personal assistant application server including a processor configured to determine a target location for a selected registered user at a predetermined time, determine a group of other registered users who are or will be physically present at the target location at the predetermined time or within a time range prior to the predetermined time, determine group health data representing a health condition of the group of other registered users, the group health data being determined based on anonymous medical records statistics for the group of other registered users stored in an aggregated medical records statistics database in communication with the electronic personal assistant application server, the anonymous medical records statistics including biometric data sensed by at least one biometric sensor associated with at least one user computing device of one of the other registered users, identify a health risk level for the target location using the group health data, generate an activity warning for the target location based on the health risk level, and send the activity warning to a client computing device of the selected registered user, the activity warning configured for presentation on the client computing device.

In this aspect, the health condition may be an infectious disease condition and the health risk level is an infectious disease risk level.

In this aspect, the group health data may also be determined based on a location history of the one of the other registered users stored in an aggregated personal assistant database in the electronic personal assistant application server.

In this aspect, the biometric sensor may be a body temperature sensor associated with one of the other registered users or a camera included in the user computing device and where the biometric data includes body temperature data.

In this aspect, the biometric data may include pulse rate data and the at least one biometric sensor is a pulse rate sensor.

In this aspect, the biometric data may include blood oxygen saturation data and the at least one biometric sensor is a pulse oximeter.

In this aspect, the target location may correspond to an event in a calendar containing a plurality of events associated with the selected registered user and may be stored in a user personal assistant database in the electronic personal assistant application server.

In this aspect, the activity warning may be configured to discourage participation in the event.

In this aspect, the processor may further configured to automatically reschedule and/or cancel the event in response to generating the activity warning.

In this aspect, the target location may be determined based on travel service reservation data corresponding to the selected registered user and may be stored in a user personal assistant database in the electronic personal assistant application server.

In this aspect, the target location may be determined based on a location history of the selected registered user and stored in a user personal assistant database in the electronic personal assistant application server.

In this aspect, the anonymous medical records statistics may include medical records of one or more of the other registered users, the medical records including medical history, medications, test results, and/or immunization status.

In this aspect, the group health data may also be determined based on search queries, location history, and event data correlated to the registered user group stored in an aggregated personal assistant database in the electronic personal assistant application server.

According to another aspect, a method for operation of a computing system is provided. The method includes at an electronic personal assistant application server, determining a target location for a selected registered user at a predetermined time, determining a group of other registered users who are or will be physically present at the target location at the predetermined time or within a time range prior to the predetermined time, determining group health data representing a health condition of the group of other registered users, the group health data being determined based on anonymous medical records statistics for the group of other registered users stored in an aggregated medical records statistics database in communication with the electronic personal assistant application server, the anonymous medical records statistics including biometric data sensed by at least one biometric sensor in at least one user computing device associated with one of the other registered users, identifying a health risk level for the target location using the group health data, generating an activity warning for the target location based on the health risk level, and sending the activity warning to a client computing device of the selected registered user, the activity warning configured for presentation on the client computing device.

In this aspect, the target location may be determined based on an event in a calendar containing a plurality of events corresponding to the selected registered user and stored in a user personal assistant database in the electronic personal assistant application server, the method further comprising automatically rescheduling and/or cancelling of the event in response to generating the activity warning.

In this aspect, the biometric data may include body temperature data, blood oxygen saturation data, and/or heart rate data.

In this aspect, the anonymous medical records statistics may include medical records of one or more of the other registered users, the medical records including medical history, medications, test results, and/or immunization status.

According to another aspect, a computing system is provided. The computing system includes an electronic personal assistant application server including a processor configured to determine a target location for a selected registered user at a predetermined time, the target location corresponding to an event in a calendar containing a plurality of events associated with the selected registered user and stored in a user personal assistant database in the electronic personal assistant application server, determine a group of other registered users who are or will be physically present at the target location at the predetermined time or within a time range prior to the predetermined time, determine group health data representing an infectious disease condition of the group of other registered users, the group health data being determined based on anonymous medical records statistics for the group of other registered users stored in an aggregated medical records statistics database in communication with the electronic personal assistant application server, the anonymous medical records statistics including biometric data sensed by at least one biometric sensor in at least one user computing device associated with one of the other registered users, identify an infectious disease risk level for the target location using the group health data, generate an activity warning for the target location based on the infectious disease risk level, and send the activity warning to a client computing device of the selected registered user, the activity warning configured for presentation on the client computing device.

In this aspect, the biometric data may include body temperature data, blood oxygen saturation data, and/or heart rate data.

In this aspect, the group health data may also be determined based on a location history of the one of the other registered users stored in an aggregated personal assistant database in the electronic personal assistant application server.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A computing system comprising:
an electronic personal assistant application server including a processor configured to:
determine a target location for a selected registered user at a predetermined future time based on one or more of positioning data of a client computing device of the selected registered user and/or future event data for the selected registered user previously stored in an electronic database accessible to the electronic personal assistant application server;
determine a group of other registered users who will be physically present at the target location at the predetermined future time or within a time range prior to the predetermined future time based on one or more of positioning data of a client computing device of each other registered user and/or event data for each other registered user previously stored in an electronic database accessible to the electronic personal assistant application server;
determine group health data representing a health condition of the group of other registered users correlated with the health condition, the group health data being determined based on anonymous medical records statistics for the group of other registered users stored in an aggregated medical records statistics database in communication with the electronic personal assistant application server, the anonymous medical records statistics including biometric data sensed by at least one biometric sensor associated with at least one user computing device of at least one of the other registered users;
identify a value of a health risk level for the target location using the group health data of the group of other registered users;
generate an activity warning for the target location based on the value of the health risk level satisfying a condition; and
send the activity warning to the client computing device of the selected registered user over a communications network, the activity warning configured for presentation on the client computing device with an indication of the target location or a future event associated with the target location.

2. The computing system of claim 1, where the health condition is an infectious disease condition and the health risk level is an infectious disease risk level.

3. The computing system of claim 2, where the group health data is also determined based on a location history of the one of the other registered users stored in an aggregated personal assistant database in the electronic personal assistant application server.

4. The computing system of claim 1, where the biometric sensor is a body temperature sensor associated with one of the other registered users or a camera included in the user computing device and where the biometric data includes body temperature data.

5. The computing system of claim 1, where the biometric data includes pulse rate data and the at least one biometric sensor is a pulse rate sensor.

6. The computing system of claim 1, where the biometric data includes blood oxygen saturation data and the at least one biometric sensor is a pulse oximeter.

7. The computing system of claim 1, where the target location corresponds to an event in a calendar containing a plurality of events associated with the selected registered user and stored in a user personal assistant database in the electronic personal assistant application server.

8. The computing system of claim 7, where the activity warning is configured to discourage participation in the event.

9. The computing system of claim 8, where the processor is further configured to automatically reschedule and/or cancel the event in response to generating the activity warning.

10. The computing system of claim 1, where the target location is determined based on travel service reservation data corresponding to the selected registered user and stored in a user personal assistant database in the electronic personal assistant application server.

11. The computing system of claim 1, where the target location is determined based on a location history of the selected registered user and stored in a user personal assistant database in the electronic personal assistant application server.

12. The computing system of claim 1, where the anonymous medical records statistics include medical records of one or more of the other registered users, the medical records including medical history, medications, test results, and/or immunization status.

13. The computing system of claim 1, where the group health data is also determined based on search queries, location history, and event data correlated to the registered user group stored in an aggregated personal assistant database in the electronic personal assistant application server.

14. A method for operation of a computing system comprising:
at an electronic personal assistant application server, determining a target location for a selected registered user at a predetermined future time;
determining a group of other registered users who will be physically present at the target location at the predetermined future time or within a time range prior to the predetermined future time based on one or more of positioning data of a client computing device of the selected registered user and/or future event data for the selected registered user previously stored in an electronic database accessible to the electronic personal assistant application server;
determining group health data representing a health condition of the group of other registered users correlated with the health condition, the group health data being determined based on anonymous medical records statistics for the group of other registered users stored in an aggregated medical records statistics database in communication with the electronic personal assistant application server, the anonymous medical records statistics including biometric data sensed by at least one biometric sensor in at least one user computing device associated with at least one of the other registered users;
identifying a value of a health risk level for the target location using the group health data of the group of other registered users;
generating an activity warning for the target location based on the value of the health risk level satisfying a condition; and
sending the activity warning to the client computing device of the selected registered user over a communication network, the activity warning configured for presentation on the client computing device with an indication of the target location or a future event associated with the target location.

15. The method of claim 14, where the target location is determined based on an event in a calendar containing a plurality of events corresponding to the selected registered user and stored in a user personal assistant database in the electronic personal assistant application server, the method further comprising automatically rescheduling and/or cancelling of the event in response to generating the activity warning.

16. The method of claim 14, where the biometric data includes body temperature data, blood oxygen saturation data, and/or heart rate data.

17. The method of claim 14, where the anonymous medical records statistics include medical records of one or more of the other registered users, the medical records including medical history, medications, test results, and/or immunization status.

18. A computing system comprising:
an electronic personal assistant application server including a processor configured to:
determine a target location for a selected registered user at a predetermined future time based on one or more of positioning data of a client computing device of the selected registered user and/or future event data for the selected registered user previously stored in an electronic database accessible to the electronic personal assistant application server;
determine a group of other registered users who will be physically present at the target location at the predetermined future time or within a time range prior to the predetermined future time based on one or more of positioning data of a client computing device of each other registered user and/or event data for each other registered user previously stored in an electronic database accessible to the electronic personal assistant application server;

determine group health data representing an infectious disease condition of the group of other registered users correlated with the health condition, the group health data being determined based on anonymous medical records statistics for the group of other registered users stored in an aggregated medical records statistics database in communication with the electronic personal assistant application server, the anonymous medical records statistics including biometric data sensed by at least one biometric sensor in at least one user computing device associated with at least one of the other registered users;

identify a value of an infectious disease risk level for the target location using the group health data of the group of other registered users;

generate an activity warning for the target location based on the value of the infectious disease risk level satisfying a condition; and send the activity warning to the client computing device of the selected registered user over a communications network, the activity warning configured for presentation on the client computing device with an indication of the target location or a future event associated with the target location.

19. The computing system of claim 18, where the biometric data includes body temperature data, blood oxygen saturation data, and/or heart rate data.

20. The computing system of claim 18, where the group health data is also determined based on a location history of the one of the other registered users stored in an aggregated personal assistant database in the electronic personal assistant application server.

* * * * *